United States Patent [19]

Boone

[11] 4,150,442
[45] Apr. 24, 1979

[54] ELBOW OR HEEL PROTECTOR

[75] Inventor: Walter S. Boone, Valdese, N.C.

[73] Assignee: Alba-Waldensian, Incorporated, Valdese, N.C.

[21] Appl. No.: 914,415

[22] Filed: Jun. 12, 1978

[51] Int. Cl.² ............... A41D 13/08; A61B 19/00
[52] U.S. Cl. ........................................ 2/16; 2/24; 2/239; 128/149; 128/165
[58] Field of Search .............. 2/16, 22, 24, 158, 159, 2/170, 239, 240, 241, 2; 128/149, 165, 153, 166

[56] References Cited

U.S. PATENT DOCUMENTS

| | | | |
|---|---|---|---|
| 1,846,835 | 2/1932 | Bruckler | 2/16 |
| 3,189,919 | 6/1965 | Chase | 2/16 |
| 3,322,118 | 5/1967 | Southerlin | 128/149 |
| 3,648,291 | 3/1972 | Pankers | 2/16 |
| 3,937,218 | 2/1976 | Gaylord, Jr. | 2/16 X |
| 3,990,440 | 11/1976 | Gaylord, Jr. | 2/24 X |

Primary Examiner—H. Hampton Hunter
Attorney, Agent, or Firm—Bell, Seltzer, Park & Gibson

[57] ABSTRACT

The present protector includes a tubular sleeve which is stretchable in both longitudinal and circumferential directions and is adapted to provide a snug fit over the arm or foot of the patient and a pad carried by the sleeve. The pad is of substantially U-shaped transverse cross-sectional configuration and substantially V-shaped longitudinal cross-sectional configuration so as to receive and cushion the patient's elbow or heel therein. The pad includes a pair of opposite side panels defining opposite sides of the U-shaped transverse cross-sectional configuration and a pair of superpositioned substantially rectangular bottom panels providing additional padding in the central portion and defining the V-shaped longitudinal cross-sectional configuration. The lower edges of the the side panels are seamed to the corresponding opposite sides of the lowermost of the superpositioned bottom panels with the opposite sides of the uppermost of the bottom panels being free of connection and covering the seams to prevent contact of the seams with the patient.

7 Claims, 8 Drawing Figures

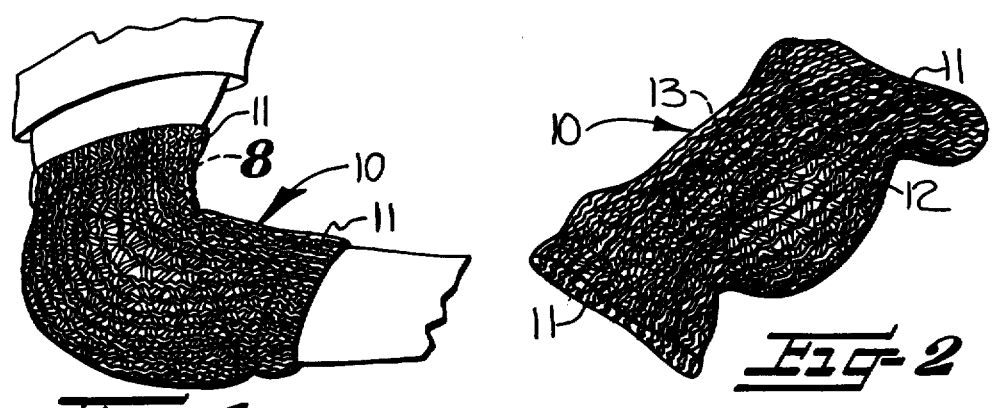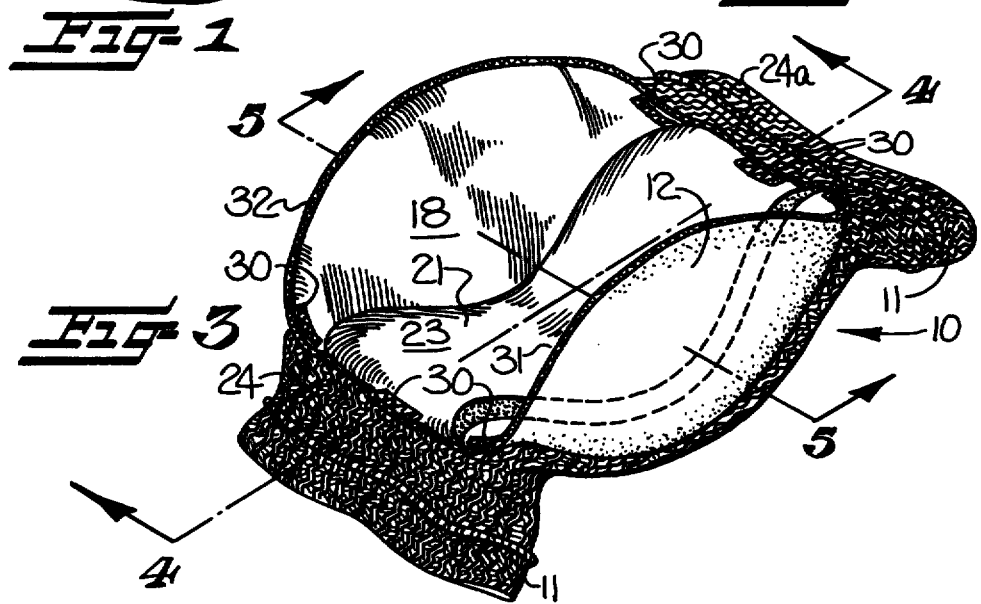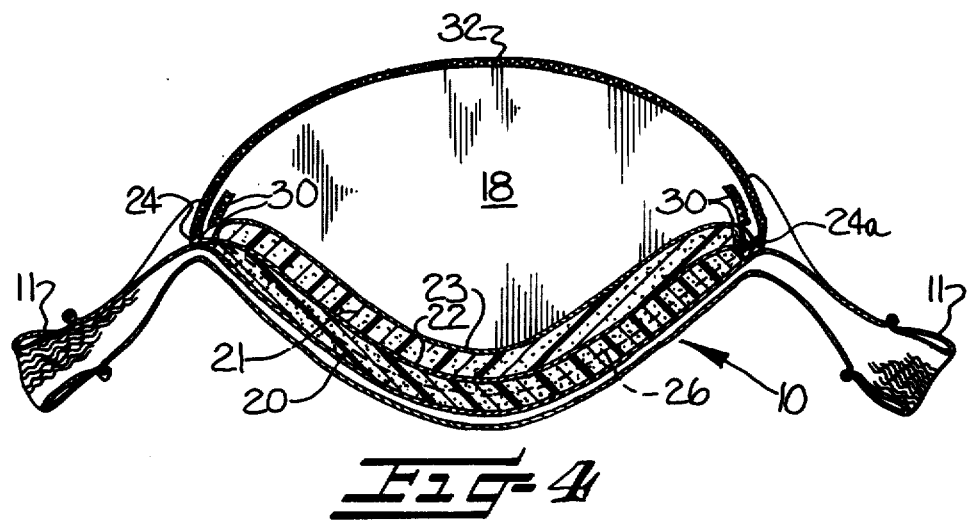

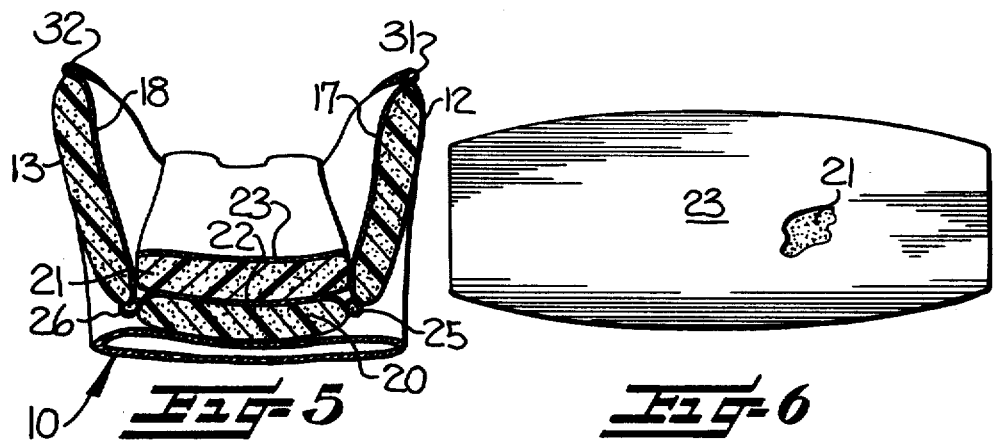
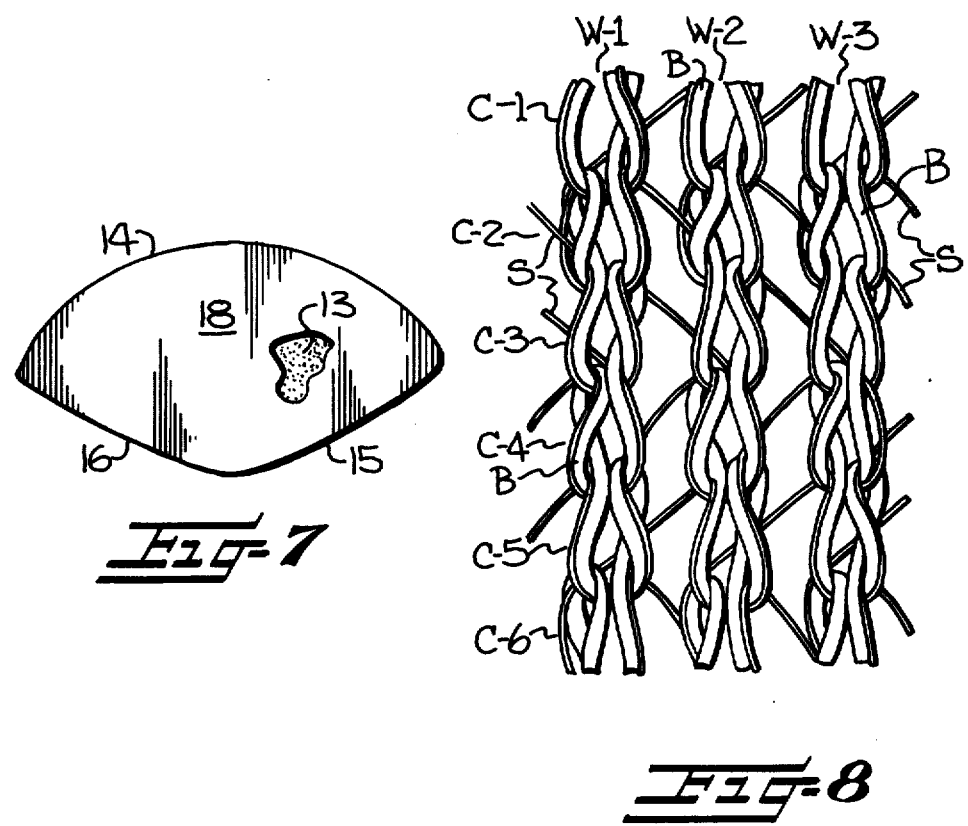

ELBOW OR HEEL PROTECTOR

This invention relates generally to an elbow or heel protector and more particularly to such a protector which includes a knitted tubular sleeve and a pad formed of seamed together pieces of foam material to provide additional padding in the central portion and to protect the patient from contact with the seams.

Various types of elbow or heel protector pads have heretofore been proposed for use by patients confined to bed for extended periods of time. These pads have been used to protect the patient from pressure and abrasive contact with the bed in an effort to aid in prevention of the development of decubitus ulcers or bedsores. Certain types of the protective pads heretofore used have included shaped pieces of foam material seamed together to form a cup or pocket for receiving the heel or elbow of the wearer. It has been found that this type of protector does not provide sufficient padding in the central portion and the seams connecting the pieces of foam material cause discomfort and abrasive contact with the patient.

With the foregoing in mind, it is an object of the present invention to provide an elbow or heel protector which includes additional padding in the central area where the greatest pressure is applied and protects the patient from contact with the seams connecting together the portions of the pad.

The elbow or heel protector of the present invention includes a tubular sleeve which is stretchable in both directions and is adapted to provide a snug fit over the arm or foot of the patient and pad means positioned within the sleeve and secured thereto to cushion the patient's elbow or heel therein. The pad means is of substantially U-shaped transverse cross-sectional configuration and substantially V-shaped longitudinal cross-sectional configuration to receive and cushion the patient's elbow or heel.

The pad means includes opposite side panels of resilient foam material defining opposite sides of the U-shaped transverse cross-sectional configuration with a soft fabric laminated to the inner surfaces of each of the side panels. Each of the side panels includes an upper peripheral edge defining substantially one-third of a circle and a pair of converging lower edges extending from the upper peripheral edge and joining each other to provide a fairly wide V-shaped lower edge. A pair of superpositioned substantially rectangular bottom panels of resilient foam material extends between the lower edges of the side panels and defines the substantially V-shaped longitudinal cross-sectional configuration. The pair of bottom panels provides additional padding in the central portion of the pad. The superpositioned bottom panels are substantially rectangular with opposite sides of the lowermost bottom panel being seamed to the corresponding lower edges of the opposite side panels. The opposite sides of the uppermost of the bottom panels are free of connection to the side panels and cover the seams connecting the lower edges of the side panels to opposite sides of the lowermost bottom panel. The uppermost bottom panel thus protects the patient from abrasive contact with the seams.

The stretchable tubular sleeve is seamless and is knit on a circular warp knitting machine and includes adjacent walewise extending stitch chains, each being knit of a textured synthetic stretchable body yarn. The adjacent stitch chains are connected together by covered spandex yarns which are interknit with the body yarn stitch chains and extend diagonally from one wale to an adjacent wale. The interconnected stitch chains provide an open knit construction to provide adequate porosity or breatheability to the sleeve.

Other objects and advantages will appear as the description proceeds when taken in connection with the accompanying drawings, in which—

FIG. 1 is a perspective view illustrating the present protector positioned on the elbow of a wearer;

FIG. 2 is a perspective view of the protector removed from the arm;

FIG. 3 is a perspective view of the pad, with the tubular stretchable sleeve being everted with the pad on the outside;

FIG. 4 is a longitudinal sectional view taken substantially along the line 4—4 in FIG. 3 and illustrating the substantially V-shaped longitudinal cross-sectional configuration of the pad;

FIG. 5 is a transverse sectional view taken substantially along the line 5—5 in FIG. 3 and illustrating the substantially U-shaped transverse cross-sectional configuration of the pad;

FIG. 6 is a plan view of one of the substantially rectangular bottom panels of resilient foam material used in forming the pad;

FIG. 7 is a plan view of one of the opposite side panels of resilient foam material used in forming the pad; and FIG. 8 is a greatly enlarged view of a fragmentary portion of the tubular sleeve, taken in the area of the dotted rectangle 8 in FIG. 1, and showing the warp knit construction thereof.

The present elbow or heel protector includes a tubular sleeve, broadly indicated at 10, which is stretchable in both longitudinal and circumferential directions and is adapted to provide a snug fit over the arm or foot of the patient. The tubular sleeve 10 is seamless and warp knit with opposite ends being turned inwardly and connected as by seams to form opposite end welts 11. The tubular sleeve 10 is of an open knit construction to provide adequate porosity or breatheability and includes spaced-apart stitch chains knit with individual wrap body yarns B, as illustrated in wales W-1, W-2 and W-3 of FIG. 8. The body yarns B are preferably textured synthetic stretchable yarns and the individual stitch chains are connected together by covered spandex yarns S which are interknit with the stitch chains of the body yarn B and extend diagonally from one wale to an adjacent wale.

It is preferred that each of the covered spandex yarns S be shogged or lapped a distance of two wales in one direction and then lapped in the reverse direction a distance of two wales. For example, it will be noted in FIG. 8 that the covered spandex yarn S which forms a stitch loop in course C-2 of wale W-1 extends downwardly and diagonally to the right and forms the next stitch loop in course C-3 of wale W-2. The spandex yarn S then extends downwardly and diagonally to the right and forms the next stitch loop in course C-4 of wale W-3. The spandex yarn S then reverses direction and is shogged to the left so that it extends downwardly and diagonally to form the next stitch loop in course C-5 of wale W-2, and then extends downwardly and diagonally to form the next stitch loop in course C-6 of wale W-1.

The present elbow or heel protector also includes pad means positioned within and secured to the sleeve 10 to receive and cushion the patient's elbow or heel. It will be noted in FIG. 5 that the pad is of substantially U-shaped transverse cross-sectional configuration in the central portion thereof, and in FIG. 4 that the pad is of substantially a wide V-shaped longitudinal cross-sectional configuration. The pad includes opposite side panels 12, 13 which define opposite sides of the U-shaped transverse cross-sectional configuration.

The opposite side panels 12, 13 are formed of resilient foam material and each of the side panels includes an upper curved peripheral edge 14 (FIG. 7) defining substantially one-third of a circle and a pair of converging lower edges 15, 16 (FIG. 7) extending from the upper edge 14 and joining each other. Thus, the lower edges 15, 16 define a wide V-shape with an included angle of approximately 120 degrees. The width of the side panel, the distance between the upper ends of the lower edges 15, 16, is 6½ inches while the height, from the medial point of the curved upper edge 14 to the juncture of the lower edges 15, 16, is 3¼ inches. The resilient foam material is preferably ⅜ of an inch thick and a fine soft textile fabric, such as tricot knit fabric, indicated at 17 and 18, is laminated to the inner surfaces of the respective side panels 12, 13.

A pair of superpositioned substantially rectangular bottom panels 20, 21, formed of pieces of resilient foam material, define the bottom of the U-shaped transverse cross-sectional configuration (FIG. 3). Each of the respective lowermost and uppermost bottom panels 20, 21 is substantially rectangular and is preferably slightly wider in the middle than at opposite ends (FIG. 4) and is provided with repective textile fabric 22, 23 laminated to the upper surfaces thereof. Opposite ends of each of the bottom panels (FIG. 6) are preferably two inches wide and opposite sides curve outwardly with the medial portion of the bottom panel being preferably three inches wide. The bottom panel is 7½ inches long.

First seam means, in the form of overedge seams 24, 24a (FIG. 3), connect together corresponding opposite ends of the superpositioned bottom panels 20, 21. Second seam means, in the form of zigzag rows of stitching 25, 26 (FIG. 5), connect together the lower edges 15, 16 of the side panels 12, 13 to the corresponding opposite sides of the lowermost of the superpositioned bottom panels 21. As illustrated in FIG. 3, the opposite sides of the uppermost bottom panel 21 are free of connection to the side panels 12, 13 and cover the seams 25, 26 to prevent abrasive contact of the patient with these seams. Also, the superpositioned bottom panels 20, 21 provide additional padding in the center and along the bottom of the pad.

The pad is secured in position in the sleeve 10 by short rows of tacking stitches in various positions at opposite ends of the pad, such as illustrated at 30 in FIGS. 1-3. It is also preferred that an overedge seam be provided along the upper peripheral edges 14 of the side panels 12, 13, as indicated at 31 and 32 in FIG. 3.

The resilient or stretchable tubular sleeve 10 may be easily drawn over the foot or hand of the patient and the pad positioned beneath the heel or elbow. The stretchable sleeve 10 maintains the pad in the proper position to provide protection for the heel or elbow without applying an objectionable amount of pressure to the arm or foot. The inner surface of the pad is smooth and is devoid of any abrasive seams which may contact the patient and the lower portion of the pad provides additional padding in the area where greatest pressure is exerted.

In the drawings and specification there has been set forth a preferred embodiment of the invention, and although specific terms are employed, they are used in a generic and descriptive sense only and not for purposes of limitation, the scope of the invention being defined in the claims.

That which is claimed is:

1. An elbow or heel protector for providing cushioning to confined bed patients and the like, said protector comprising
   (a) a tubular sleeve stretchable in both longitudinal and circumferential directions and being adapted to provide a snug fit over the arm or foot of the patient,
   (b) pad means positioned within said sleeve to receive and cushion the patient's elbow or heel, said pad means being of substantially U-shaped transverse cross-sectional configuration in the central portion thereof and including
      (1) opposite side panels of resilient foam material defining opposite sides of said U-shaped cross-sectional configuration, each of said side panels including an upper peripheral edge and a pair of converging lower edges extending from said upper peripheral edge,
      (2) a pair of superpositioned substantially rectangular bottom panels of resilient foam material including opposite sides and opposite ends and defining the bottom of said U-shaped cross-sectional configuration,
      (3) first seam means connecting together corresponding opposite ends of said superpositioned substantially rectangular bottom panels of resilient foam material, and
      (4) second seam means connecting said lower edges of said opposite side panels to the corresponding opposite sides of the lowermost of said superpositioned substantially rectangular bottom panels of resiient foam material, the opposite sides of the uppermost of said substantially rectangular bottom panels of resilient foam material being free of connection to said side panels and covering said second seam means to prevent contact of the patient with said second seam means, and
   (c) means securing said pad means in position within said sleeve.

2. An elbow or heel protector according to claim 1 wherein said securing means for said pad means comprises stitching at opposite ends of said pad means and penetrating said pad means and said sleeve.

3. An elbow or heel protector according to claim 1 including textile material laminated to and covering the inner surfaces of said resilient foam material forming opposite side panels, and textile material laminated to and covering the upper surface of the uppermost of said pair of superpositioned substantially rectangular bottom panels of resilient foam material.

4. An elbow or heel protector according to claim 1 including an overedge seam extending along said upper peripheral edges of said opposite side panels and across the ends of said pair of superpositioned substantially rectangular bottom panels of resilient foam material.

5. An elbow or heel protector according to claim 1 wherein said tubular sleeve is seamless and warp knit.

6. An elbow or heel protector according to claim 5 wherein said warp knit seamless tubular sleeve includes adjacent walewise extending stitch chains knit of textured synthetic stretchable body yarn, and spandex yarns interknit with said stitch chains and extending diagonally between and connecting together adjacent stitch chains.

7. An elbow or heel protector according to claim 1 wherein said upper peripheral edge of each of said side panels defines substantially one-third of a circle and wherein said lower edges of each of said side panels converge at an included angle of approximately 120 degrees.

* * * * *